United States Patent [19]
Saxon et al.

[11] Patent Number: 6,043,345
[45] Date of Patent: Mar. 28, 2000

[54] IGE ISOFORMS AND METHODS OF USE

[75] Inventors: Andrew Saxon, Santa Monica; Ke Zhang, Los Angeles, both of Calif.; Edward E. Max, Bethesda, Md.; Jeffrey B. Lyczak; Sherie L. Morrison, both of Los Angeles, Calif.

[73] Assignee: The Regents of the University of California, Oakland, Calif.

[21] Appl. No.: 08/601,184

[22] Filed: Feb. 14, 1996

Related U.S. Application Data

[63] Continuation-in-part of application No. 08/037,579, Mar. 24, 1993, Pat. No. 5,552,537.

[51] Int. Cl.[7] .................................................. C07K 16/00
[52] U.S. Cl. ................... 530/387.1; 530/324; 536/23.53
[58] Field of Search ................................. 530/324, 386; 536/23.53

[56] References Cited

U.S. PATENT DOCUMENTS 5,254,671  10/1993  Chang ..................................... 530/324

OTHER PUBLICATIONS

Peng, C. 1992. J. Immunology, 148:129–136.
Hellman L. 1993. Eur. J. Immunology 23:159–167.
Batista et al., "Characterization and Expression of Alternatively Spliced IgE Heavy Chain Transcripts Produced by Peripheral Blood Lymphocytes," J. of Immunology (1995), 209–218.
Zhang et al., "Complex Alternative RNA Splicing of ε–Immunoglobulin Transcripts Produces mRNAs Encoding Four Potential Secreted Protein Isoforms," J. of Biological Chemistry (Jan. 1994), 269:456–462.
Efremov et al., "Molecular Analysis of IgE H–Chain Transcripts Expressed in Vivo by Peripheral Blood Lymphocytes from Normal and Atopic Individuals," J. of Immunology (Aug. 1993), 151:2195–2207.
Peng et al., "A New Isoform of Human Membrane–Bound IgE," J. of Immunology (Jan. 1992), 148:129–136.
Seno et al., "Molecular Cloning and Nucleotide Sequencing of Human Immunoglobulin ε Chain cDNA," Nucleic Acids Research (1983), 11:719–726.
Flanagan and Rabbits, "The Sequence of a Human Immunoglobulin Episilon Heavy Chain Constant Region Gene, and Evidence for Three Non–Allelic Genes," The EMBO Journal (1982), 1:655–660.
Max et al., "Duplication and Deletion in the Human Immunoglobulin ε Genes," Cell (Jun. 1982), 29:691–699.
Diaz–Sanchez, D., et al. "Differential Regulation of Alternative 3' Splicing of ε Messenger RNA Variants" J. of Immunology (1995), 155:1930–1941.
Lyczak, J., et al. "Expression of Novel Secreted Isoforms of Human Immunoglobulin E Proteins" J. Biological Chemistry (Feb. 1996), 271:3428–3436.
Diaz–Sanchez, D., et al. "Diesel Exhaust Particles Induce Local IgE Production In Vivo and Alter the Pattern of IgE Messenger RNA Isoforms" J. of Clinical Investigation (Oct. 1994) 94:1417–1425.
Zhang, K., et al. "Germ–Line Human Epsilon Heavy Chain Gene RNA Transcripts Utilize The Full Range of Alternative 3' Splicing Seen in Productive ε mRNA" Immunology (1995), 85:228–235.

*Primary Examiner*—Lila Feisee
*Assistant Examiner*—Minh-Tam Davis
*Attorney, Agent, or Firm*—Richard F. Trecartin; Mark T. Kresnak; Flehr Hohbach Test Albritton and Herbert LLP

[57] ABSTRACT

Methods and compositions are provided relating to novel IgE isoforms and their use in immune hypersensitivity diagnosis and treatment. The compositions include transcription and translation products of the immunoglobulin epsilon locus, specific probes for epsilon transcription products, and compounds that specifically bind epitopes of epsilon translation products. Novel products of the epsilon locus include the following transcription products and translation products thereof: CH4-M2", CH4'-CH5-M1'-M2, CH4'-CH5-M2', CH4'-CH5-M2Δ and CH4-M2'. Such epsilon products, specific probes and binding compounds find use in methods and kits for immune hypersensitivity diagnosis and treatment.

4 Claims, 4 Drawing Sheets

FIG. 1A

```
                                                                                                              M2
                                                                                                              M2'
                                                                            90         100
                                                                    ValGlnArgPhe      M2
CATGTGGGCACCCACCTCCAGGGCCCAGCCAGGGCAGGGGTTGGGCAGAGCCAGAGCGCCCTGACCCACGCCCTCCCCTCAGGTGCAGCGGTTC
                                                                    GlyAlaAlaVal     M2'

110         120         130         140         150         160         170         180         190         200
LeuSerAlaThrArgGlnGlyProGlnThrThrAsnValLeuGlnProHisAla***
CTCTCAGCCACGCGGCAGGGGAGGCCCAGACCCTGACTCCTCCAGACCTCCTCGACTACACCAACGTCCTCCAGCCCCACGCCTAGGCCGACTCACGTCCACCAGGC
ProLeuSerHisAlaAlaGlyGluAlaGlyProAlaProArgLeuHisGlnArgProAlaProProArgLeuGlyArgGlyProLeuThrProLeuHisGlnAla   M2'

210         220         230         240         250         260         270         280         290         300
CCAGCTTTTTCTGCCAGCCGCCTCCCTCGGGCTGACCGCCTGCCCTGGGAAAAGGGAAGCAGAAGAAAAGGGGCAGAAGGTCACTAC
GlnLeuPheLeuCysGlnLeuArgLeuSerArgAlaAlaProCysProGlyTrpGlyGluLysGlyLysGlyAlaGlnGlyHisTyr 310         320         330         340         350         360         370         380         390         400
TGTGGGCTGATGGCCAGTGAACCTGAGGAGGGGGTGCTGCTAGCCGTTCTGAGCTCATCCCAGGCCCCTGGGTCTCCGGGTCACTCTG
CysGlyLeuMetAlaSerGluProGluGluGlyValAlaAlaSerArgSerGluLeuIleProGlyProTrpValSerGlySerLeuPro 410         420         430         440         450         460         470         480         490         500
                        GluSerSerArgGlyGlyCys***
CGTGTCGTCCCTTCAACAGAGTCATCGAGGAGGGGTGCTGCTAGCCGTTCTGAGCTCATCCCAGGCCCCTGGGTCTCCGGGTCACTCTGACT    M2'
ProCysLeuGlnGlnSerHisArgGlyGlyValAlaAlaSerArgSerGluLeuIleProGlyProTrpValSerGlySerLeuProPhe***   M2'
                                                                            7

510         520         530         540         550         560         570         580         590         600
CGTGTCGTCCCTTCAACAGAGTCATCGAGGAGGGGTGCTGCTAGCCGTTCTGAGCTCATCCCAGGCCCCTGGGTCTCCGGGTCACTCTGACT 610         620         630         640         650         660         670         680         690         700
GTACAATCACCAAAAGCCAAGGAGGGCCCGGCACCCAGCCCAACACCAGCCTCCAGCCACAGTCTGCGTCCCCACCCGTCCCCCAAGCCTCACCCCAGCCT

CGGTCTGACCCCTTCTAGCCCTGAGATCCAAGTGCCTGGCATCCCCGTCCCCCAAGCCTCACCCACCCCAGACCTTCTTTCCCTTCACCCACCCCTCCTGCCACCC
                                  8
```

IGE ISOFORMS AND METHODS OF USE

This is a continuation-in-part of U.S. Ser. No. 08/037,579, filed Mar. 24, 1993, now U.S. Pat. No. 5,552,537.

The research described in the subject application was supported at least in part by grants Al15251, A15352 (CIRID at UCLA), CA30515, CA43503 and CA16858 from the National Institutes of Health. The U.S. government may have rights in any patent issuing on this application.

INTRODUCTION

1. Technical Field

The field of this invention is IgE isoform-mediated immune hypersensitivity diagnostics and therapeutics.

2. Background

The IgE isotype, defined by the immunoglobulin epsilon heavy chain, plays a complex role in the immune system that includes combating parasitic infections. IgE appears to mediate immediate-type hypersensitivity (allergic) reactions, including various allergic reactions such as hay fever, extrinsic asthma, and allergies to certain foods, drugs, etc., by virtue of its ability to bind with high affinity epsilon-specific Fc receptors on certain cells such as mast cells and basophils. It appears that the binding of allergen triggers crosslinking of the bound IgE and their Fc receptors, which in turn triggers release of a host of pharmacologic and inflammatory mediators, such as histamine and interleukins. Accordingly, while IgE represents only a minute fraction of antibody present in circulation, the concentration of this isotype seems to correlate with some allergic diseases, or at least their severity, and assaying for the presence of allergen-specific IgE is used for diagnosing immediate-type hypersensitivity.

Northern blot analysis of RNA from human myeloma and hybridoma lines secreting Ig other than IgE generally reveal two bands, corresponding to transcripts encoding either a membrane-bound or secreted Ig protein. These two RNA species appear to result from alternative splicing that either includes or excludes a sequence encoding a peptide, the "transmembrane sequence", responsible for membrane anchoring. Recent publications report the identification of a family of epsilon mRNA species generated by novel RNA splicing at the 3' end. Two of these encoding proteins with complete membrane sequences are membrane bound forms. In addition to the conventional epsilon mRNA for secreted IgE, four other mRNAs contain sequences that encode either partial membrane sequences or no membrane sequences at all, suggesting the existence of as many as four additional secreted forms.

3. Relevant Literature

The nucleotide sequence of the murine immunoglobulin epsilon gene is disclosed in Ishida et al. (1982) *EMBO J.* 1:1117; and the human epsilon constant region locus in Max et al. (1982) *Cell* 29:691. IgE isoforms are described in Saxon et aL. (1991) *J. Immunol.* 147:4000; Peng et al. (1992) *J. Immunol.* 148:129–136; Zhang et al. (1992) *J. Exp. Med.* 176:233–243; and Hellman (1993) *Eur. J. Immunol.* 23:159–167.

SUMMARY OF THE INVENTION

Methods and compositions relating to novel IgE isoforms and their use in immune hypersensitivity diagnosis and treatment are provided. The compositions include transcription and translation products of the immunoglobulin epsilon locus, specific probes for epsilon transcription products, and compounds that specifically bind epitopes of epsilon translation products. Functional IgE antibody molecules are produced having novel constant region sequences. Novel products of the epsilon locus include the transcription products and translation products shown in the table of relevant sequences. Such epsilon products, specific probes and binding compounds find use in methods and kits for immune hypersensitivity diagnosis and treatment.

TABLE OF RELEVANT SEQUENCES

| Common Name | DNA Sequence | Amino Acid Sequence |
|---|---|---|
| CH4 | SEQ ID NO:1, residues 3–323 | SEQ ID NO:2 |
| CH4' | SEQ ID NO:1, residues 3–217 | SEQ ID NO:2 residues 1–72 |
| CH4" | SEQ ID NO:1, residues 218–323 | SEQ ID NO:2 residues 73–109 |
| CH5 | SEQ ID NO:1, residues 359–440 | SEQ ID NO:3 |
| M2 | SEQ ID NO:4, residues 89–169 | SEQ ID NO:5 |
| M2' | SEQ ID NO:4, residues 88–495 | SEQ ID NO:7 |
| M2" | SEQ ID NO:4, residues 420–443 | SEQ ID NO:6 |

Splice Products

CH4' SEQ ID NO:2 residues 1–72-CH5 SEQ ID NO: 3
(IgEψCH4)
CH4 SEQ ID NO:2-M2" SEQ ID NO:6
(IgEtp)
CH4 SEQ ID NO:2-M2' SEQ ID NO:7
(IgE grandé)

BRIEF DESCRIPTION OF THE DRAWINGS

FIG. 1B. Human ε membrane exon 2' (nucleotides 89–498) and its 3' untranslated region sequence is shown. The amino acid sequences generated from the various alternative splicing products in different reading frames are also given. The bold brackets define the boundary of the splice acceptor sites described. The amino acid translation shown above nucleotide sequence 89–169 represents the translation of the M2 exon, while that from nucleotide position 421 represents the amino acid sequence of the M2" form. The amino acid translation shown below nucleotide sequence 88–495 represents the M2' reading frame. The location of the oligonucleotides used for primers or probes are given as in FIG. 1A.

FIG. 2. Diagrammatic summary of 3' ends of ε RNA species. A schematic genomic DNA map for CH4 and the ε membrane exon region sequence is shown at the top. All the sequence confirmed splicing products are shown to the right of their corresponding names and compared with the classic secreted form that is listed on the top. The table at right indicates which forms are membrane (m) vs secreted (s) and shows the number of amino acids longer or shorter than the classical secreted form. The bold horizontal bars represent translated sequence. The asterisks show the position of in-frame termination codons, the thin horizontal lines represent 3' untranslated sequence.

In FIG. 3A the amount of $H_2L_2$ secreted is expressed as a percentage of the total heavy and light chain produced during the pulse. In FIG. 3B, the amount of $H_2L$ and HL secreted is expressed as a percentage of the total heavy and light chain produced during the pulse.

DESCRIPTION OF THE SPECIFIC EMBODIMENTS

The compositions of the invention include isolated novel IgE heavy chain constant region (epsilon) nucleotide sequences and polypeptides comprising an epitope specific to a translation product encoded by such epsilon nucleotide sequences. Polypeptides of interest include novel functional IgE molecules. Included are novel epsilon exons and novel alternatively spliced transcripts of previously identified epsilon exons that were not predicted by the prior art. The novel epsilon nucleotide sequences include CH5, a novel epsilon exon, and M2" and CH4' where CH4" is joined to other than CH4", novel alternatively spliced epsilon transcript portions, as described herein or sequences of substantial sequence or structural homology thereto.

For consideration of splicing variants, the conventional epsilon CH4 domain (SEQ ID NO:1, residues 3–323) may be broken down into CH4' (SEQ ID NO:1, residues 3–217) and CH4" (SEQ ID NO:1, residues 218–323). By the term CH4' joined to other than CH4" it is intended that the nucleotide sequence described as CH4' may be joined to any or no other nucleotide sequence, other than that portion of CH4 normally found in the unrearranged chromosome 3' of CH4'. CH4' is preferably joined to at least a portion of another epsilon nucleotide sequence, except CH4", and more preferably at least a portion of CH5. By joined is meant that the sequences form a continuous polynucleotide sequence, though the joined portions may be separated by intervening sequences. As will be clear from the figures and following disclosure, the coding sequence of M2" has a reading frame shift as compared with M2'. As used herein, M2" translation products derive from the disclosed M2" reading frame, i.e. the disclosed M2" codon sequence.

An epitope of a translation product is a three-dimensional structural conformation presented by the translation product that distinguishes the translation product from other epsilon translation products. While such epitopes are functionally defined in terms of a spatial conformation, typically, such epitopes are identified by amino acid sequence homology with the disclosed sequences or with antibodies, preferably monoclonal antibodies, that are capable of distinguishing one epsilon translation product from other epsilon translation products. Specific binding to such an epitope is conveniently shown by generally known solid phase or competitive binding assays. Specific binding will generally have a binding affinity of $10^{-6}$ M, preferably $10^{-8}$ M and more preferably $10^{-10}$ M under optimized conditions and temperature.

The polypeptides of the invention include peptides encoded by novel epsilon nucleotide sequences, are generally at least about 8 amino acids in length, preferably at least 20 amino acids in length and preferably less than about 1,000 amino acids. In addition to an epitope of an epsilon translation product, the polypeptides will frequently include most or all of a polypeptide epitope encoded by an epsilon nucleotide sequence and may comprise up to an entire IgE immunoglobulin or complex containing IgE. In addition, the polypeptides may be fused, for instance by recombinant, enzymatic, or chemical methods, to other chemical groups such as saccharides, lipids, peptides or polypeptide domains. Useful fusion partners include labels, cytotoxins, cytokines such as lymphokines, drugs such as immunosuppressive agents and molecules to enhance stability when used in culture or in vivo, to ease transport across membranes, to direct the epsilon encoded domain(s) to a particular site or cell type, for ease of administration, or to modulate the binding characteristics.

An isolated nucleic acid sequence is present as other than a naturally occurring chromosome or transcript in its natural state and typically is removed from at least some of the nucleotide sequences with which it is normally associated with on a natural chromosome. A partially pure nucleic acid composition constitutes at least about 5%, preferably at least about 50%, and more preferably at least about 90% by weight of total nucleic acid present in a given fraction. The nucleic acids of the invention, other than those used in PCR amplification, are usually at least about 60 bp and usually less than about 6 kb in length. The PCR primers are generally between about 5 and 1 K nucleotides, and preferably between about 10 and 100 nucleotides in length.

Epsilon nucleic acid sequences may be modified by transitions, transversions, deletions, insertions, or other modifications, genomic sequences, flanking sequences, including regulatory and other non-transcribed sequences of the disclosed epsilon sequences, RNA and DNA antisense sequences complementary to the disclosed epsilon sequences, sequences encoding xenogeneic homologs of the disclosed sequences and sequences comprising synthetic nucleotides. Typically, the invention's epsilon sequences are associated with heterologous sequences such as regulatory sequences, e.g. promoters, enhancers, response elements, signal sequences, polyadenylations sequences, variable region sequences, etc., introns, noncoding regions, etc. The sequences may be modified with a label providing for identification or isolation. Exemplary labels include radioisotopes, fluorescers, biotinylation, etc.

For expression, the DNA sequences may be inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may be prokaryotes or eukaryotes, particularly *E. coli*; *B. subtilis;* yeast cells; mammalian cells; e.g. Cos cells, HeLa cells, myeloma or hybridoma cells, Sp2/0, CHO, L(tk—), primary cultures; insect cells; *Xenopus laevis* oocytes; and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, which may be constitutive or inducible, the gene encoding the subject methyltransferase or fragment thereof, and a transcriptional termination region. Of particular interest is the use of sequences which allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, where the vectors will normally be characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker that is chosen will be selected in accordance with the nature of the host, where in some cases, complementation may be employed with auxotrophic hosts, e.g. bacteria, yeast. Introduction of the DNA construct may be by any convenient means, e.g. conjugation, calcium-precipitated DNA, electroporation, fusion, transfection, infection with viral vectors, etc.

The subject nucleotide sequences are used to produce functional IgE proteins. As used herein, functional IgE molecules are characterized by the ability to bind antigen specifically, generally at an affinity of greater than $10^{-6}$ M, more usually having an affinity of greater than about $10^{-8}$ M. A functional antibody binding site requires both a heavy (H) chain, which is $\epsilon$ in the subject invention, and a light (L) chain, which may be either $\kappa$ or $\lambda$. In most cases the HL dimer will form a tetramer of $H_2L_2$. However, functional antigen binding may be produced with the HL dimeric form. Functional IgE antibodies may be secreted, or membrane bound.

The subject epsilon constant regions, particularly CH4'-CH5 (IgEψCH4); CH4-M2" (IgEtp); and CH4-M2' (IgE grande) may be joined to various immunoglobulin variable regions by methods known in the art, particularly through recombinant DNA technology. PCR may be used to generate fragments or novel sites for restriction endonucleases that are useful in constructing chimeric sequences for expression. The light chains may be isolated from immunoglobulin producing cells, or various known sequences may be used. It will be understood by one of skill in the art that a wide range of variable regions have been shown to function with different constant regions.

Of particular interest is the production of the subject epsilon polypeptides in the form of secreted, functional antibodies. In most cases it is preferable to introduce both heavy and light chain expression constructs into the host cell, although the two chains may be produced separately and assembled in vitro if desired. The epsilon and light chain genes may be on a single vector, or each chain may be on a separate vector.

It has been found that the production of functional IgE molecules will vary with the host cell line. A preferred host cell is a non-immunoglobulin producing mammalian cell. In one embodiment of the subject invention, a non-immunoglobulin producing myeloma cell line is used as a host cell, e.g. Sp2/0. Whether a cell line is useful for the production of functional secreted IgE may be determined by empirical analysis. For example, an expression construct comprising a complete epsilon chain may be used to transfect the cell line, together with a light chain expression vector. The transfected cells are then grown in culture, the medium collected, and assayed for the presence of secreted IgE. Various methods are known in the art for immunoglobulin quantitation, including ELISA with an IgE specific capture reagent, binding to the cognate antigen, etc. Those cell lines that are positive in such an assay are suitable for the production of functional IgE.

An isolated polypeptide or nucleic acid is unaccompanied by at least some of the material with which it is associated in its natural state. Generally, an isolated polypeptide constitutes at least about 1%, preferably at least about 10%, and more preferably at least about 50% by weight of the total protein in a given sample. Where the isolated polypeptide is an antibody molecules, either HL or $H_2L_2$, the light chain will included as a portion of the isolated protein product. Included in the polypeptide weight are alternative forms such as differentially glycosylated or phosphorylated or otherwise post-translationally modified forms. By pure polypeptide is intended at least about 90%, preferably at least 95%, and most preferably at least about 99% by weight of the total protein present in a sample.

Epsilon oligonucleotides are also used to identify other immunoglobulin epsilon sequences. For example, the disclosed nucleic acids are labeled and used to screen cDNA libraries at low stringency to identify similar cDNAs that encode proteins with related domains. Additionally, related immunoglobulin domains are isolated by PCR amplification primers as described herein or degenerate oligonucleotide probes derived from epsilon peptide sequences. PCR primers are generally between 4 and 1000 bp, preferably between 6 and 100 bp, more preferably between 10 and 50 bp in length and primer pairs usually separated by less than about 2 kb. Other useful cloning, expression, and genetic manipulation techniques for practicing the inventions disclosed herein are described in the following exemplification or are otherwise known to those skilled in the art and familiar with the methods herein or found in standard manuals such as *Molecular Cloning, A Laboratory Manual* (2nd Ed., Sambrook, Fritsch and Maniatis, Cold Spring Harbor) and *Current Protocols in Molecular Biology* (Eds. Ausubel, Brent, Kingston, Moore, Seidman, Smith and Struhl, Greene Publ. Assoc., Wiley-lnterscience, NY, N.Y., 1992).

Substantial sequence homology means at least 50%, preferably at least 70% and more preferably at least 90% shared sequence identity with the disclosed epsilon sequences. A substantially homologous nucleic acid sequence hybridizes to a disclosed sequence under low stringency conditions, for example, at 50° C. and 6X SSC (0.9 M saline/0.09 M sodium citrate) and remains bound when subject to washing at 55° C. with 1X SSC.

The invention provides a wide variety of compounds and agents that specifically bind a translation product of the disclosed sequences. Typically, such compounds and agents are identified by screening large numbers of compounds for specific binding to the disclosed epsilon encoded epitopes. The invention also provides for compounds or agents that are capable of influencing the relative transcription or translation of the IgE isoforms disclosed herein. These regulatory agents are identified by cell-based in vitro assays of isoform transcription or translation. Such agents provide pharmaceuticals for modulating the IgE isoform expression of a host.

Typically, prospective agents are screened from libraries of synthetic or natural compounds. For example, numerous means are available for random and directed synthesis of saccharide, peptide, and nucleic acid based compounds, see, e.g. Lam et al., (1991) Nature 354, 82–86. Alternatively, libraries of natural compounds in the form of bacterial, fungal, plant and animal extracts are available or readily producible. Additionally, natural and synthetically produced libraries and compounds are readily modified through conventional chemical, physical, and biochemical means.

Useful agents are found within numerous chemical classes, though typically they are organic compounds; preferably small organic compounds. Small organic compounds have a molecular weight of more than 50 yet less than about 2,500, preferably less than about 500. Exemplary classes include peptides, saccharides, steroids, and the like. Selected agents may be modified to enhance efficacy, stability, pharmaceutical compatibility, and the like.

Other useful epsilon peptide specific binding compounds include IgE isoform specific binding proteins. As discussed below, cellular responses usually distinguish IgE isoforms on the basis of differential binding to cellular proteins such as Fc receptors and other IgE binding proteins. Thus the isoforms and peptides disclosed herein are used to affinity purify a variety of cellular and serum IgE binding proteins. Such IgE binding proteins in turn find use as agents for modulating immune responses. Methods for affinity purifying IgE binding proteins are known in the art or otherwise disclosed or referenced herein.

Specific polyclonal or monoclonal antibodies that specifically bind the disclosed epsilon encoded epitopes are conveniently made using the compositions disclosed herein. For example, immunogenic peptides according to the sequences disclosed herein are conveniently made by chemical synthesis, recombinant techniques, biosynthesized, etc. Preferred peptides are readily identified from the sequences disclosed herein using techniques such as hydrophobicity plots as described in Zhang et al. (1992), supra. These peptides may be conjugated to a variety of carriers such as KLH, etc. Accordingly, antibodies that specifically recognize each IgE isoform are provided. Detailed methods for making specific antibodies, immunization protocols, monoclonal antibodies, etc are found in Harlow and Lane, *Antibodies, A Laboratory Manual,* Cold Spring Harbor Laboratory, 1988, other references cited herein, as well as immunological and hybridoma technologies known to those in the art.

The expression of IgE isoforms and transcripts thereof disclosed herein provide biochemical and ultimately biological consequences. For example, the replacement of the carboxy portion of CH4 with CH5 creates an unusual immunoglobulin domain containing only one of the two conserved Ig domain cysteine residues and adds a uniquely positioned cysteine. Accordingly, the normal intramolecular disulfide bonding characteristic of previously characterized Ig domain is not possible. Similarly, isoforms containing the disclosed M2" sequence generally have a terminal cysteine residue. Consequently, this isoform demonstrates differential propensities toward forming homo- and hetero-dimer and multimers through disulfide linkages with the terminal cysteine residue. Such structural consequences in turn provide CH5 and M2" containing IgE isoforms with differential ability to bind Fc receptors and participate in immunesensitivity responses.

Additionally, the isoforms disclosed herein present disparate targets for posttranslational modifications such as phosphorylation and glycosylation. For example, some isoforms differ in their glycosylation patterns, in turn providing for differential binding to ligand-like IgE binding proteins (see *Biochemistry* (1990) 29:8093–8100). Through their differential ability to bind other cellular components, the isoforms disclosed herein provide disparate ability to mediate a broad range of biochemical and cellular responses.

In addition, the epsilon transcripts disclosed herein also provide functional distinctions. For example, three structurally distinct transcripts are disclosed that nevertheless provide for the same peptide coding sequence. The different messages provide for variations in nuclear translocation, stability, transcription product localization, etc. In turn, differences in mRNA stability provide for expression efficiency by variations in translation product copy number and differential localizations provide for differential access to posttranslational modification enzymes and cellular export machinery.

Accordingly, the epsilon transcription and translation products disclosed herein provide convenient targets for modifying IgE-mediated cellular and physiological function. More specifically, since the differential expression of the disclosed epsilon sequences relates to IgE-mediated immune hypersensitivity conditions and propensity, epsilon-encoded epitope-specific compounds or agents and nucleic acids encoding epsilon encoded epitopes and probes thereto find use in diagnosing and treating such conditions.

Suitable hosts include human, pets such as dogs, cats, rabbits, exotic birds, etc., and farm animals such as horses. Specimens may be biological fluids, tissues, cells, or fractions and preparations thereof. Preferred specimens are derived from blood and include whole blood and fractions thereof including cellular fractions, serum, plasma, etc. Specimens may be treated or prepared in a variety of ways, e.g. blood-derived specimens may be treated with anticoagulants such as heparin and are commonly diluted with a buffered medium.

For diagnostic uses, host specimens are screened for the presence of one or more epsilon transcription or translation products both as total amount of the specific product (e.g. total circulating M2" IgE) or as amount of antigen-specific IgE isoform (e.g. amount of M2"-IgE against ragweed). Diagnosis is premised on the identification of polypeptides comprising an epitope of a translation product of an epsilon sequence described herein or transcripts encoding such an epitope. Employing the invention's epsilon translation product-specific compounds, specimens may be classed in terms of the IgE isoforms reflected by the identified epitopes of epsilon translation products. Thus, the relative concentrations of the various IgE isoforms (total and antigen specific) in a specimen are determined. Where clinical correlates are not yet established, panels of isoform profiles are readily used to demonstrate correlations to physiological conditions such as immune hypersensitivity, immune disease, tolerance, etc. that are used in subsequent diagnosis. Antigen-specific isoforms are generally assayed by contacting a specimen with suspect allergen/antigen and identifying IgE-allergen/antigen complexes, e.g. by ELISA.

A wide variety of techniques may be used for assaying the epsilon isoform compositions of a specimen with specific compounds. In a preferred embodiment, antibodies specific for given epsilon encoded epitopes are used in otherwise conventional immunoassays for measuring isoforms in a sample. Diagnosis may also encompass ascertaining the specificity of the isoform classes. For example, the diagnostic antibodies described above are used to separate the various IgE isoform classes according to conventional affinity binding methods. Thus, effector allergen specific isoforms can be identified.

The relative proportions of various cell types bearing particular isoforms can also be determined. For example, many IgE isoforms comprising the epsilon encoded translation products described herein will be secreted forms, lacking membrane anchoring domains. These isoforms present differential abilities to bind to cellular Fc receptors and IgE binding proteins. When cellular bound, the isoforms are used to identify and hence permit targeting of, or selection/separation of, cells bearing epsilon specific Fc receptors, or specific classes thereof. Such cell types include macrophages, mast cells, basophils and activated T cells. The epsilon epitope-specific antibodies also find use in quantifying and determining the relative proportions of B cells bearing particular isoforms, usually transmembrane isoforms.

Such cellular profiles can help characterize the allergic status of the individual. The method generally entails contacting specific antibodies with a host specimen including leukocytes; to be tested under conditions that permit the antibodies to bind IgE-bearing cells in the specimen. Subsequently, the cells are examined for antibody binding, by for example, immunofluorescence. Accordingly, the methods and compositions disclosed herein provide for profiling soluble, transmembrane, and Fc bound IgE isoforms, IgE isoform-specific Fc receptors, and cell types bearing various IgE isoform-specific Fc receptors.

Alternatively, diagnosis can be obtained by using various hybridization-based techniques such as PCR and Northern blotting to identify epsilon transcripts. Suitable techniques for PCR amplification of the epsilon transcripts of the invention are set out in the exemplification below or references cited herein. Of particular interest are primer pairs that specifically amplify the novel epsilon exons and spliced products disclosed herein. More particularly preferred are primers that are substantially homologous with epsilon exon splicing junctions. By junctions is meant the nucleotide sequences immediately up and downstream of the splice sites. Generally, junctions comprise at least 3 and preferably at least 6 nucleotides on each side of a splice site. For example, primers, at least a portion of which overlap the CH4'-CH5 and the CH4-M2" junctions, can be used to amplify and identify mRNA molecules containing these splice cites. By primer portion is meant at least about 12, preferably at least about 16 nucleotides of a primer. By overlap is meant that the primer and target site are sufficiently complementary that primer hybridization is specific enough to amplify the target sequences within standard PCR reaction conditions. Typically, the hybridizing primer portion and homologous strand are at least about 80% identical.

Accordingly, by selecting primers for specific exon amplification and employing a series of PCR reactions or by using multiple sets of primers simultaneously, convenient analysis of the epsilon exon profile of a specimen is provided. Additional protocols for Northern blot hybridizations and PCR reactions may be found in standard manuals such as *Molecular Cloning, A Laboratory Manual* (2nd Ed., Sambrook, Fritsch and Maniatis, Cold Spring Harbor), and *Current Protocols in Molecular Biology* (Eds. Ausubel, Brent, Kingston, Moore, Seidman, Smith and Struhl, Greene Publ. Assoc., Wiley-lnterscience, NY, N.Y., 1992).

The methods and compositions herein also find use therapeutically in the treatment of IgE-mediated hypersensitivity. The epsilon epitope-specific compound/agents (e.g. antibodies) may be used as immune function effector agents, as carriers for drugs, cytokines, cytotoxic agents, etc. For example, the cytotoxic antibody conjugates may be used to reduce or eliminate certain IgE-bearing cells by cytolysis or other regulatory immune mechanisms.

Where antibodies are administered therapeutically, it is desirable to minimize the likelihood of an immunogenic or allergenic response by using human antibodies, chimeric antibodies, human expression vectors to produce fragments of human antibodies or antibodies wherein only the antigen combining site is non-human. While intact antibodies are commonly used, the antibodies may be modified in a variety of ways, by enzymatic cleavage to provide fragments, reduction of disulfide linkages, and the like. Antibody therapy may also be used in conjunction with conventional desensitization immunotherapy or enhanced with factors that augment ADCC activities such as GM-CSF or M-CSF.

In additions, polypeptides comprising epsilon-encoded epitopes themselves find therapeutic use. Peptides thereof may be used to interfere with hypersensitivity reactions and onsets thereof. For example, classes of epsilon-specific Fc receptors on certain mast cells and basophils can be blocked with non-crosslinking compounds and prevent allergic reaction. Such treatments may be administered prophylactically or, especially in cases of anaphylaxis, acutely.

For therapeutic uses, the compositions and selected agents disclosed herein may be administered by any convenient way that will depend upon the nature of the compound/ agent, the purpose and frequency of the treatment. For small molecular weight agents, oral administration is preferred and enteric coatings may be indicated where the compound is not expected to retain activity after exposure to the stomach environment. Generally the amount administered will be empirically determined, typically in the range of about 0.1 to 1000 ug/kg of recipient.

Large proteins are preferably administered parenterally or systemically, conveniently in a physiologically acceptable carrier, e.g., phosphate buffered saline, saline, deionized water, or the like. Some agents, such as antibodies can also be administered nasally. Typically, compositions are added to a retained physiological fluid such as blood. Generally, the amount administered will be empirically determined, typically in the range of about 10 to 1000 $\mu$g/kg of the recipient. Other additives may be included, such as stabilizers, bactericides, etc. These additives will be present in conventional amounts.

The invention provides for diagnostic kits for obtaining IgE isoform and IgE isoform-specific Fc receptor profiles for hypersensitivity or allergy testing. These kits may include containers, e.g. microtiter plates. In one type of kit the container walls are pre-coated with a first IgG class antibody specific for one or more IgE isoforms. In a second kit, prospective allergen(s) is/are immobilized, preferably on the surface of a multi-well plate. In both cases, a separately packaged second, preferably polyclonal, antibody conjugated to a label and specific to one or more IgE epitopes is provided. Where enzyme-labeled antibody is provided, substrate and reaction stopping reagents may also be provided.

Alternative kits are based on the identification of mRNA species amplifiable by PCR from a specimen. Preferred primers are substantially homologous to mRNA regions which overlap two epsilon exons or alternatively spliced exon portions such as the CH4'-CH5 junction and the CH4-M2" junctions. A preferred kit contains sufficient primers to simultaneously amplify any of all the diagnostically useful epsilon exons from a specimen. Other useful junctions include CH4-M1', CH4-M2", M1-M2,M1'-M2, CH3-CH5, CH5 joined to the various M regions, etc.

The following examples are offered by way of illustration and not by way of limitation.

EXPERIMENTAL

Materials and Methods

Cell lines and cell cultures. The human IgE secreting cell line AF-10 was maintained in complete RPMI 1640 medium as previously described in Saxon et al. (1991) *J. Immunol.* 147:4000. EBV transformed IL4-induced ε-secreting human B cell lines 2C4/F3 and 2C10/F9 (described in Thyphronitis et al. (1991) *J. Immunol.* 146:1496) were maintained in complete RPMI 1640 supplemented with 50 mM Hepes and $3 \times 10^{-5}$ M 2-mercaptoethanol (Sigma). Freshly purified human B cells were isolated from tonsils and purified by the methods described previously in Saxon et al. (1976) *J Immunol Methods* 12:285. For induction of productive ε transcripts, purified B cells ($1 \times 10^6$ cell/ml) were cultured for 7 days in the presence or absence of 100 U/ml recombinant IL-4 plus 0.1 μg/ml of anti-CD40 mAb G28-5 (See Zhang et al. (1991) *J Immunol.* 146:1836). Spontaneously IgE producing human B cells were obtained from patients with the Hyper-IgE immunodeficiency syndrome or atopic dermatitis.

Figure 1A:
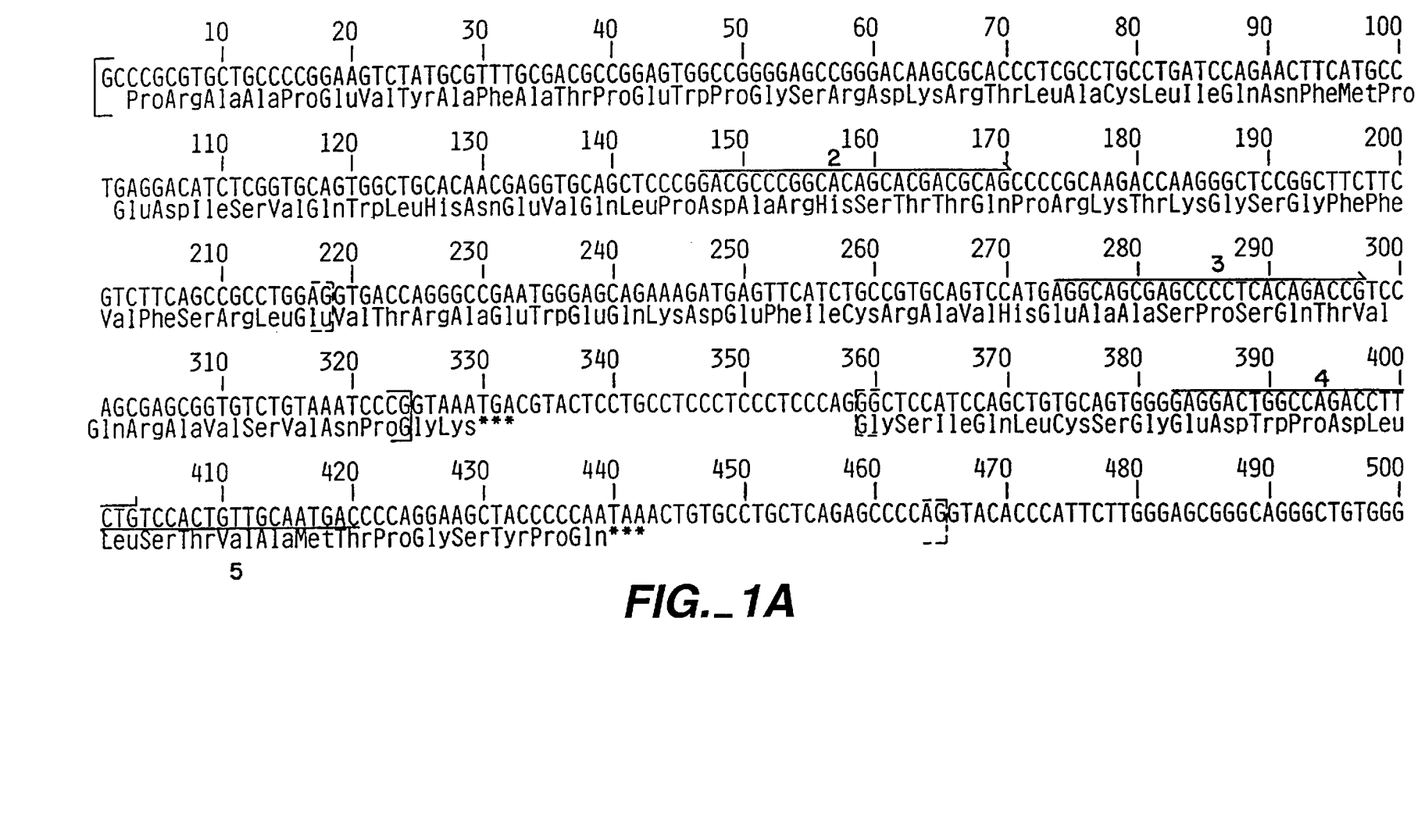
FIG. 1A. The genomic sequence of human epsilon CH4 (nucleotides 1–323) and its 3' flanking sequence is presented, and the amino acid translation for the CH4 domain and CH4'-CH5 splicing product is given below the nucleotide sequence. The bold brackets represent donor or acceptor sites of the full length CH4 and the dashed brackets define the boundary of CH4'-CH5 splicing. The oligonucleotides used for primers or probes are also shown; the arrow under the sequence indicates that the oligo was designed based on the strand complementary to that shown here.
Figure 1B:
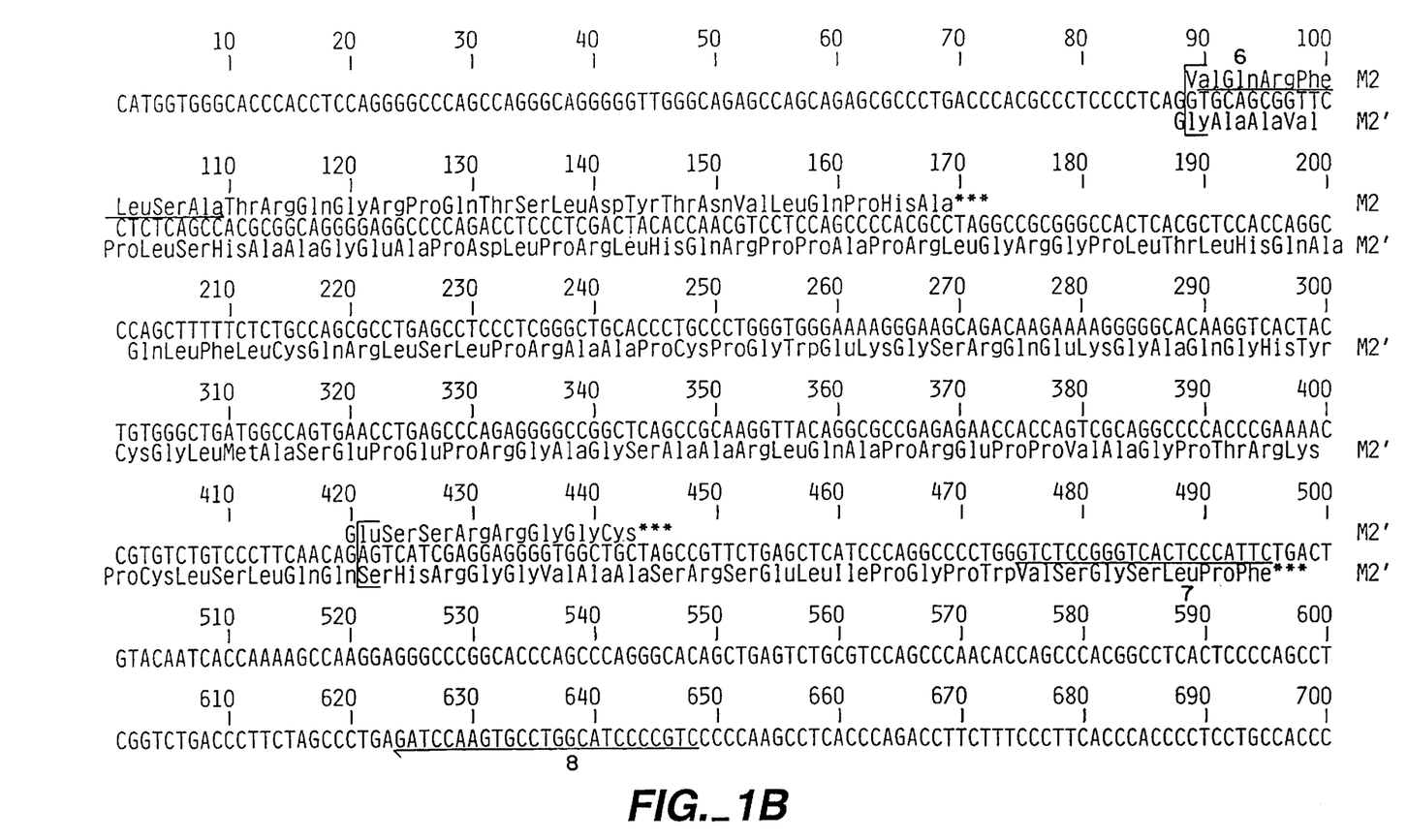

Amplification. RNA was isolated from the various cells and reverse transcribed by standard methods as described by Zhang et al. (1992) *J. Exp. Med.* 176:233. Pairs of PCR primers were designed to detect different forms of ε mRNA containing membrane exon sequences (Table 1 and FIG. 1). The same primer used by Zhang et al. (1992), was used in the present work but is referred to by a different name herein. The primer is listed under both names in Table 1. Some primers were designed with terminal enzyme restriction sites to facilitate cloning and sequencing of PCR products. PCR amplifications were performed for 40 cycles under the conditions described in Zhang et al. (1992).

Southern blot analysis of PCR products. PCR products were electrophoresed on 1.5% agarose gels. DNA was transferred to nylon membranes (Nytran, Schleicher & Schuell Inc., Keene, N.H.) in 0.4 M NaOH. Blots were analyzed by probing with end-labelled oligonucleotides corresponding to various regions of the genomic sequence shown in FIG. 1. Hybridization with kinased oligonucleotide probes was performed as described in Zhang et al. (1992).

Analysis of amplified ε cDNAs. PCR products were digested with Cla I and Sal I, purified by agarose gel electrophoresis, and then ligated into BluescriptR (Stratagene, La Jolla, Calif.) vector that had been prepared by Cla I and Sal I digestion and treatment with alkaline phosphatase. Plasmid minipreps were analyzed by restriction digestion, agarose gel electrophoresis and hybridization to internal probes. The inserts of the selected clones were sequenced on both strands by the dideoxy termination method using a sequencing kit purchased from USB (USB, Cleveland, Ohio).

Results

Splicing of CH4 to a novel splice acceptor site inside the M2' exon. To explain the multiple IgE bands appearing on Western blots of secreted human IgE, we considered the possibility that splicing of ε immunoglobulin heavy chain RNAs might be more complex than previously described. In our earlier RT-PCR studies of alternative ε RNA splicing we had observed a small DNA fragment that we had considered a possible PCR artifact since it did not hybridize to several probes internal to the exons M1 or M2, Zhang et al. (1992). To explore the possibility that this band reflected a genuine splice form containing sequence downstream from the previously tested M2 probes, we subjected RNA from the IgE secreting cell line AF-10 to RT-PCR using the primer pair 3–9 (Table 1 and FIGS. 1 and 2), and included a far downstream probe in our hybridization analysis. Amplifications with this primer pair consistently generated five bands with RNA derived from all IgE+ cells tested. All five of these products hybridized to a probe located downstream of the M2' exon (oligo 7, Table 1), but only the larger (upper) four bands hybridized to an M2' internal probe located in the beginning of the M2' exon (oligo 6, Table 1). These results suggested that one form of ε mRNA, represented by band 5, resulted from splicing to a novel acceptor site inside the M2' exon between oligo 6 and 7.

Because PCR-generated heteroduplex formation between alternative spliced products may cause artifactual bands, Zhang et al. (1992), we investigated whether any of the observed bands represented heteroduplexes. When DNA corresponding to bands 2 and 4 was recovered and subcloned, DNA from band 2 always gave subclones identical to band 1 and band 3, while band 4 always gave subclones identical to bands 3 and 5. No subclones with inserts the size of band 2 or 4 were ever obtained in three experiments. On the other hand, band 2 and band 4 could be generated on gels by reamplifying the DNA templates from mixtures of the subcloned band 1, 3 and 5. Amplification of templates corresponding to a single subclone never produced band 2 or 4. These experiments indicated that bands 1, 3 and 5 represent true individual PCR products, while bands 2 and 4 are PCR-generated heteroduplexes.

Of the three true PCR products amplified with primer pair 3 and 9, bands 1 and 3 had the correct size and hybridization characteristics expected for two RNA splice forms that we previously described: CH4-M1'-M2 and CH4-M2", respectively. These identities were confirmed by sequence analysis. Sequencing further showed that the band 5 products from RNAs derived from all of our IgE+ cells were identical, reflecting an RNA spliced from the usual donor site near the 3'end of CH4 to a novel acceptor site in the terminal portion of the M2' exon (nucleotide 421 in FIG. 2). The sequence at this position is a typical splice acceptor site. This novel spliced RNA (designated CH4-M2") has a one nucleotide reading frame shift compared with the frame of the same DNA sequence in the previously described CH4-M2' form. As a result, translation of the new CH4-M2" mRNA should terminate at the TAG at position 444 of FIG. 2.

Figure 2:
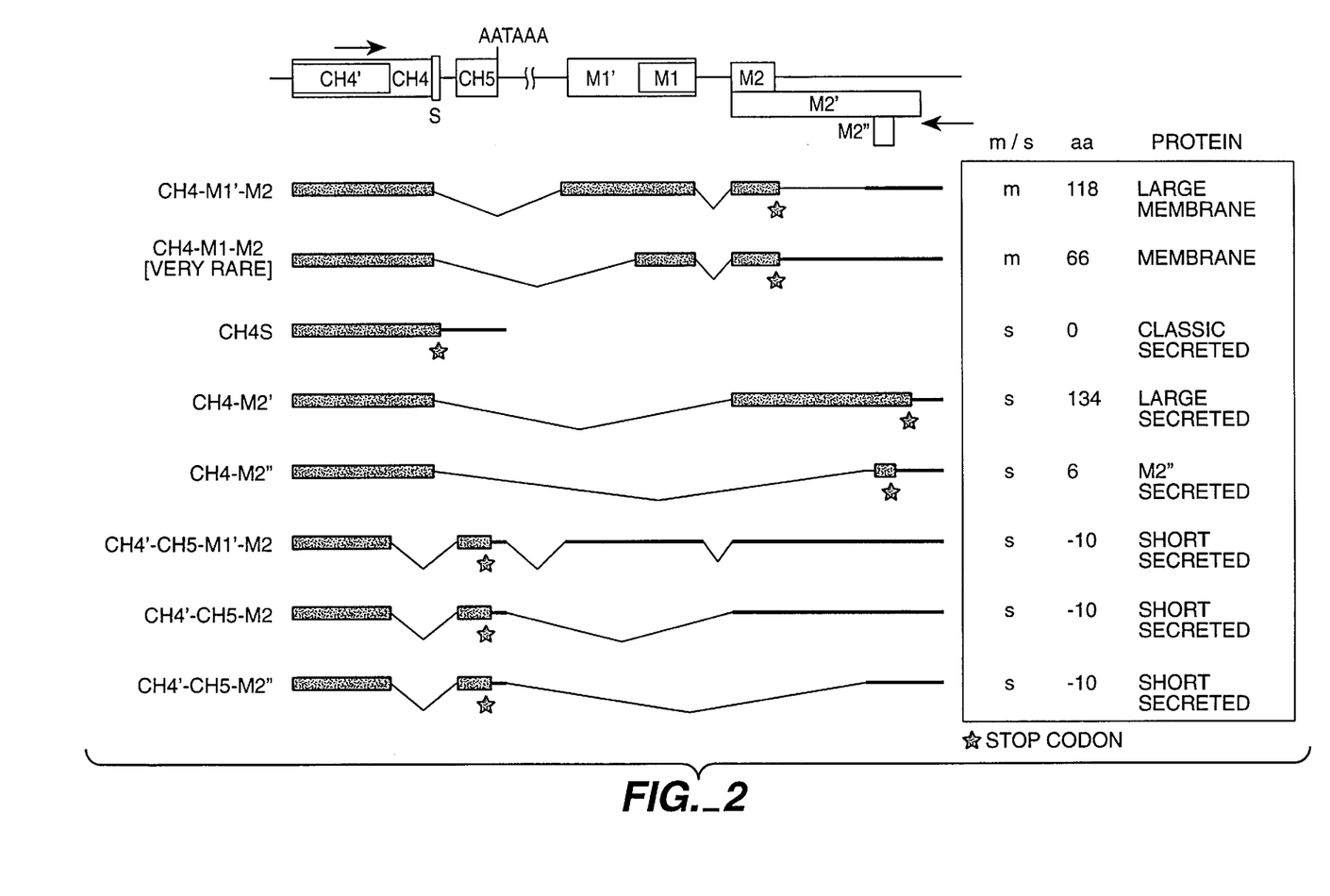

The protein encoded by this RNA would be secreted (as it lacks the membrane anchor sequence of the Ml exon), and in its structure the two C-terminal acids of the "classical" secreted form would be replaced with a novel eight residue C-terminus (FIG. 2).

Three novel ε RNA transcripts that define a new exon: CH5. In our previous analysis of ε RNA isoforms, we described a single RT-PCR subclone representing an RNA that spliced from a novel donor site within CH4 (nucleotide 218 in FIG. 1) to a novel splice acceptor site located in the 3' untranslated region sequence downstream of CH4 (nucleotide 359 of FIG. 1). This clone, whose structure was designated CH4'-l-M1'-M2, Zhang et aL. (1992), was originally isolated from the same PCR band as the abundant CH4-M1'-M2 splice product. The existence of two PCR products in the same band was explained by the nearly identical sizes of these two products, as the length of the segment designated "I" (107 bp) almost exactly compensates for the DNA lost from the 3' end of the truncated CH4' (106 bp). Our current evidence (described below) indicates that this novel splice is found in all IgE+ cell samples tested, defining a new exon that we have renamed CH5 (to avoid confusion with the "I" exon upstream of the ε switch region).

To investigate RNA forms with this splice, amplification products obtained using the 2(IVm)-9 primer pair were analyzed by Southern blotting and hybridization with oligonucleotide probes specific either for CH5 (probe 4) or for the 3' end of CH4, which is absent from CH4' (probe 3). Since the IVm primer sequence is 5' to the splice donor site at the 3' end of CH4', this primer should amplify RNA forms with an intact CH4 exon as well as the CH4'-CH5 RNAs. As in the amplification described above, three major bands were produced, along with intermediate-sized bands that appear to be heteroduplex artifacts on the basis of experiments similar to those described above. Strikingly, all five bands hybridized to both probe 3 and probe 4, suggesting that each band might represent a mixture of CH4 and CH4'-CH5 amplification products. This interpretation was supported by cloning the PCR bands 1, 3 and 5; each band yielded some clones hybridizing to probe 3 and others hybridizing to probe 4, but no clones were obtained that hybridized to both probes. Sequence analysis of representative clones containing CH5 showed that this exon always terminated with the same 5' and 3' ends, and that the sequences downstream of CH5 reflected the same three splice acceptor sites observed in the RNA forms that contain intact CH4 and no CH5. These CH5-containing clones thus defined three new RNA splice forms: CH4'-CH5-M1'-M2 (band 1), CH4'-CH5-M2' (band 3) and CH4'-CH5-M2" (band 5). All of these would encode the same protein, because translation of all would terminate within CH5 at the TAA codon at position 440 of FIG. 1. Clones hybridizing to probe 3 were shown by sequence analysis to reflect the intact CH4 exon spliced to the same three downstream splice acceptor sites, representing splice forms reported earlier (CH4-M1'-M2 and CH4-M2') or described above (CH4-M2"). (Neither the rare CH4-M1-M2 form nor a CH4'-CH5'-M1-M2 counterpart was observed in these experiments; nor did we detect any products splicing from the donor site at the 3' end of M1 or M1' to M2".) The existence of the CH4'-CH5 product is still further confirmed by amplification of cDNA with the primer set 1 and 5, a set of primers that are able to simultaneously amplify both the constitutive CH4S product (where S states for secreted terminus) and the alternatively spliced CH4'-CH5 products. These results demonstrate that indeed both predicted PCR products were observed and hybridized to an internal probe for both CH4 and CH4' (oligo 2), but only the larger band hybridized to oligo 3.

EXAMPLE 2

Expression of IgE Isoforms

Materials and Methods

Figure 3A:
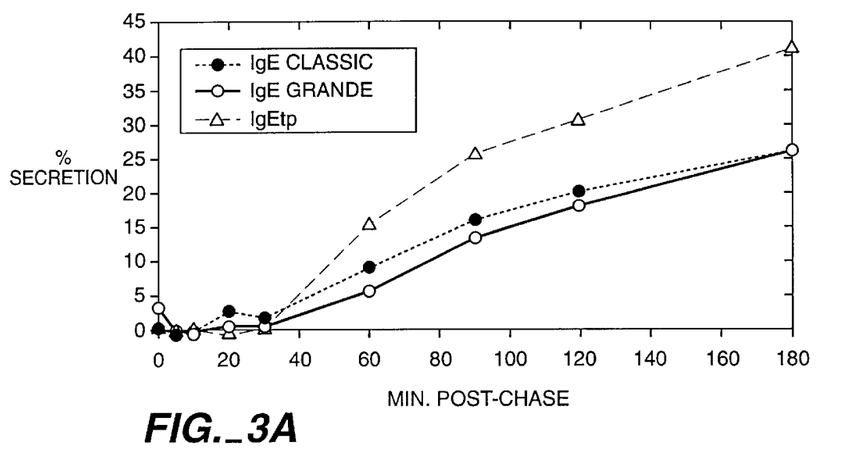
FIGS. 3A and 3B show the kinetics of secretion of IgE isoforms. Data are from densitometric analysis of pulse chase experiments.
Figure 3B:
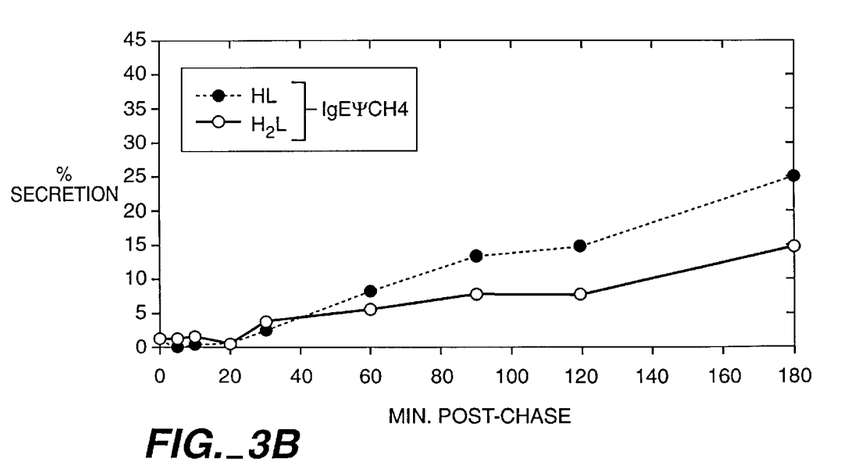

Vectors and Proteins. To create isoform specific epsilon constructs, a portion of the human epsilon gene encoding $C_\epsilon 1$ through $C_\epsilon 4$ was fused in frame to three RT-PCR clones. The RT-PCR clones span the downstream sequences resulting from alternative splicing events, as well as a portion of Ce4 (shown in FIG. 3). RT-PCR cloning of 3' portions of the various epsilon mRNAs is described above.

Isoform-specific epsilon chains were created by first using PCR mutagenesis to create novel Xbal or Nhel restriction sites within the $C_\epsilon 4$ coding region of each of these RT-PCR clones, and an EcoRl site at the 3' end of each clone (before the polyadenylation addition signal). PCR mutagenesis was then used to create the identical mutations within the $C_\epsilon 4$ exon of the human genomic epsilon gene. The Xbal site was created at arginine 520, the Nhe site was created at alanine 543. In all cases introduction of the restriction site did not alter the amino acid sequence. The Xbal or Nhel sites were then used to fuse the various downstream sequences with the epsilon gene. The 3'-untranslated region (UTR) from human γ3 heavy chain gene had been provided with an EcoRl site 5' of the polyadenylation addition signal and was substituted for the 3'-UTR of the human epsilon gene by ligation at the EcoRl sites created at the 3' ends of the RT-PCR clones. The genes encoding the different epsilon isoforms were then cloned into pSV2 gpt containing the coding sequence for a heavy chain variable domain specific for the hapten dansyl chloride under the control of the Ig heavy chain promoter and Ig heavy chain enhancer. This was done by ligation at the BamHl site at the 3' end of the 3'-UTR and by ligation of the Xhol site immediately 5' of the $C_\epsilon 1$ exon with a Sall site 3' of the heavy chain enhancer in the expression vector. The Sall and Xhol sites were destroyed in the ligation. The anti-dansyl light chain used is a chimeric kappa chain consisting of a murine variable domain and a human $C_k$ domain.

Cells. Sp2/0 and J558L murine myeloma cells and various transfectants thereof were carried in Iscove's modified Dulbecco's medium (Irvine Scientific, Santa Ana, Calif.) containing 5% bovine calf serum (Hyclone, Logan, Utah). A stable anti-dansyl light chain producing line (TWS) was established from Sp2/0 cells as previously described. Stable IgE-producing cell lines were created by electroporation of the isoform-specific heavy chain in the pSV2 gpt expression vector into TWS. Briefly, 10 μg of DNA linearized at the BamHl site was added to $10^7$ TWS cells in 0.9 ml phosphate-buffered saline, and the cells were pulsed at 200 V with 980 microfarads in a 0.4-cm electrode gap cuvette (Bio-Rad). Stable transfectants were selected for growth in medium containing 42 μg/ml hypoxanthine, 1 μg/ml xanthine, and 2.5 μg/ml mycophenolic acid. Clones producing IgE were identified by ELISA using plates coated with dansyl chloride. Supernatants from clones were added to wells, and bound protein was detected using goat anti-human kappa chain conjugated to alkaline phosphatase (Sigma). Nonsecreting transfectants of J558L were identified by lysis of $5\times10^6$ cells in lysis buffer (lysis buffer=0.5% Nonidet P40, 50 mM Tris, pH 7.0, 150 mM NaCI, and 5 mM EDTA) and analysis of lysates by ELISA using plates coated with the anti-human IgE monoclonal antibody CLA 7.12. Bound protein was detected using goat anti-human epsilon chain conjugated to alkaline phosphatase (Sigma).

Isoform-specific ELISA. The anti-IgE monoclonal antibody CIA-7.12, which recognizes an epitope at the $C_\epsilon 2/C_\epsilon 3$ boundary was used as the coating reagent, as previously described. After blocking, the cell culture supernatant containing expressed IgE isoforms were incubated for 2 h at room temperature. ClA-7.12 or a 1:500 dilution of α-2331, a rabbit antiserum generated against a peptide corresponding to the COOH-terminal 10 amino acids of CH4-M2'(3) was then added to the microplate and incubated for 2 h at room temperature followed by a 2 h incubation with goat anti-rabbit IgG conjugated to alkaline phosphatase (Sigma).

Western Blotting. Western blotting analysis has been previously described. Briefly, the expressed IgE isoforms were immunoprecipitated from the cell culture supernatants with monoclonal antibody CIA-7.12 coupled to Sepharose 4B (Pharmacia Biotech, Inc.). After transfer, the nylon membrane was blocked by 4% bovine serum albumin/phosphate-buffered saline/Tween for 4 h at room temperature. For ε protein detection, the blot was probed with goat anti-human IgE (ε chain specific) conjugated to alkaline phosphatase (Kirkegaard and Perry Laboratories, Inc., Gaithersburg, Md.). For detection of CH4-M2', the blot was incubated with 1:200 diluted α-2331 overnight at 4° C. followed by a 2 h incubation at room temperature with anti-rabbit IgG conjugated to alkaline phosphatase (Sigma). Color development was performed with an alkaline phosphatase conjugate substrate kit (Bio-Rad) as described by the manufacturer.

Metabolic Labeling, Precipitation and SDS-polyacrylamide Gel Electrophoresis. 4–10×10$^6$ transfected cells were washed twice in 2 ml of methionine-deficient Dulbecco's modified Eagle medium (Mediatech, Harndon, Vt.), resuspended in 1 ml of methionine-deficient Dulbecco's modified Eagle medium containing [$^{35}$S]methionine (15 µCi/10$^8$ cells) (ICN, Irvine, Calif.), and incubated at 37° C. for 6–18 h. Supernatant from the cell culture was cleared of debris by centrifugation for 5 min. at 225×g at 4° C.

To precipitate the Ig protein, 2.5 µl of rabbit anti-human Fab anti-serum (R27) was added to each culture supernatant, and the supernatant was incubated at 4° C. for 2–18 h. 100 µl of IgGsorb Staph A (The Enzyme Center, Malden, Mass.) was then added, and the supernatant was incubated at 4° C. for 15 min to 1 h. Immune complexes were spun through a pad of 30% sucrose+0.15% SDS+0.5X NDET (1XNDET= 1% Nonidet P-40, 0.4% deoxycholate, 0.5 mM EDTA, and 10 mM Tris, pH 7.4), and the pellet was washed sequentially in 300 µl of NDET+0.3% SDS and 400 µl of distilled water. The pellet was then resuspended in sample loading buffer (loading buffer=25 mM Tris, pH 8.7, 2% SDS, 10% glycerol and 0.1 µg/ml bromphenol blue) and boiled for 2 min. The samples were analyzed on polyacrylamide gels. For two-dimensional gel analysis, samples were first electrophoresed on 5% polyacrylamide gels, and the lane containing the sample of interest was excised and incubated in sample loading buffer containing 5% dithiothrietol (Boehringer Mannheim) for 20 min at room temperature. The lane was then embedded in 12.5% polyacrylamide. Electrophoresis was then done as described.

Pulse-Chase. 2–8×10$^6$ transfected cells/time point were washed twice in 2 ml of methionine-deficient Dulbecco's modified Eagle medium. Washed cells were then incubated in 2 ml of methionine-deficient Dulbecco's modified Eagle medium for 1 h at 37° C. to deplete the cells of intracellular methionine. Cells were pulsed with [$^{35}$S]methionine (ICN) (15 µCi/10$^6$ cells) for 5 min at 37° C. and then chased with 8 ml of chase medium that had been prewarmed to 37 φC. (chase medium=Iscove's modified Dulbecco's medium (Irvine Scientific)+10% bovine calf serum (Hyclone)+3.35 mg/ml unlabeled methionine (Schwartz-Mann, Orangeberg, N.Y.) ). At various time points, 1 ml aliquots were removed to tubes containing an equal volume of prechilled phosphate buffered saline on ice. Trichloroacetic acid-precipitable radioactivity was determined at varius time points to confirm that the amount of nonradioactive methionine added was sufficient to prevent continued [$^{35}$S]methionine incorporation during the 3-h chase.

Cells were separated from the supernatant by centrifugation for 5 min at 225×g at 4° C. Cell lysates were prepared by resuspending the cell pellet in 0.5 ml of NDET, centrifuging at 4° C. for 15 min at 15,000×g and discarding the pellet. IgE was precipitated from the supernatants and cell lysates with a mixture of rabbit anti-human Fab (R27 antiserum) and rabbit anti-human epsilon (IcN) as described above.

For densitometry of IgE assembly intermediates, nonreducing gels from pulse-chase experiments were visualized by autoradiography and scanned on a Hewlett/Packard Scanjet llcx scanner. The images were analyzed at 600 dots/inch using the NIH image software.

Results

Production of Genetically Determined IgE Isoform-specific Transfectomas. FIG. 3 illustrates the strategy used for generating constructs encoding specific isoforms of human IgE. RT-PCR products encompassing the 3' portion of $C_\epsilon 4$ and sequences downstream were mutagenized by PCR to introduce either an Xbal site or an Nhel site within the $C_\epsilon 4$ portion of the RT-PCR clone without altering the amino acid sequence of the encoded protein. The identical restriction sites were also engineered in a separate construct contaning the $C_\epsilon 1$ through $C_\epsilon 4$ exons. Mutagenesis was also used to introduce an EcoRl sites after the termination codons of the RT-PCR clones. The RT-PCR clones containing 3' coding sequences were fused to the sequences for $C_\epsilon 1$ through $C_\epsilon 4$ at the Xbal or the Nhel site. A polyadenylation addition signal was provided by ligation to an EcoRl site previously engineered immediately upstream of the polyadenylation signal in the 3' UTR from human IgG3. The resulting constructs were subcloned into pSV2 gpt containing an exon encoding a variable heavy chain domain specific for the hapten dansyl chloride. The expression vectors were then transfected into an Sp2/0-derived cell line previously transfected with a chimeric light chain comprised of a murine anti-dansyl $V_L$ domain and a human $C_k$ domain were transfected into the J558L cell lin, which synthesizes a murine λ light chain.

Analysis of Proteins Secreted by the isoform-Determined IgE Transfectomas. Transfectomas secreting IgE classic, CH4-M2' and CH4-M2" produce a protein of approximately 190 kDa that reduces upon treatment with 2-mercaptoethanol to a heavy chain of approximately 75 kDa and a light chain of approximately 25 kDa. This indicates that these isoforms are secreted as fully assembled $H_2L_2$ molecules. As expected, IgE classic and CH4-M2" migrate with identical mobilities, whereas CH4-M2' migrates slightly slower. The transfectoma expressing CH4'-CH5 secretes HL, which migrates as a broad band that is 75–90 kDa as well as light chain of approximately 25 kDa under nonreducing conditions. A minor component migrating at approximately 150 kDa that is apparently $H_2L$ is detectable only in some experiments. The heavy chain of CH4'-CH5 migrates somewhat faster than the heavy chain of the other three isoforms. This difference is not due to glycosylation because it is still evident when the transfectomas are labeled in the presence of tunicamycin, an inhibitor of N-linked glycosylation. However, the diffuse migration of the 75–90 kDa species does indicate heterogeneous glycosylation of the epsilon heavy chain because it is no longer evident when the transfectoma is labeled in the presence of tunicamycin. A panel of 10 transfectomas expressing CH4'-CH5 all showed this pattern of assembly. The identities of the 75–90 and 150 kDa species as HL and $H_2L$, respectively, are supported by two-dimensional SDS-polyacrylamide gel electrophoresis analysis. The species that migrates as 75–90 kDa and 150 kDa in the first dimension dissociate into heavy and light chains when run reduced in the second dimension. Furthermore, the 75–90 kDa species both immunoprecipitates and reacts in Western blots with epsilon-specific monoclonal and polyclonal antibodies. In addition to fully assembled $H_2L_2$ molecules, all four lines secrete free light chain and light chain dimers, as is frequently observed in this expression system.

Because the protein secreted by the cell line producing CH4-M2' does not migrate as slowly as one would predict, based on the amino acid translation, experiments were undertaken to verify that the protein was indeed complete and intact. Initially, the expression construct for CH4-M2' was subjected to extensive restriction analysis, which showed that the entire coding region had been retained in the construct. Due to concern that the novel 136-amino acid tail of the CH4-M2' could be post-translationally cleaved, the protein was analyzed by ELISA and Western blotting using antibodies specific for the COOH terminal ten amino acids of CH4-M2' (α-2332). As expected, both IgE classic and CH4-M2' were recognized by CIA-7.12, whereas α-2331 recognizes CH4-M2" but failed to recognize classic secreted IgE. Neither CIA-7.12 or a-2331 recognized an IgG control. Recognition of CH4-M2' by α-2331 indicates that the large secreted terminus is not removed by proteolytic processing. In addition, recognition of CH4-M2' by CIA-7.12 indicates that the $C_\epsilon 2$-$C_\epsilon 3$ interface is intact; the ability of CH4-M2' to bind antigen verifies that the $V_H$ is present. The data is shown in Table 1.

of the isoforms examined. In the case of CH4'-CH5 the HL form constitutes the majority of IgE secreted as $H_2L$. By 3 h after the pulse, approximately 20% of the labeled Ig is secreted in the HL form, whereas only 10% is secreted as $H_2L$. All four transfectants synthesize excess light chain that is secreted as free L and $L_2$ dimers.

Two species of 50 and 200 kDa co-precipitate with intracellular CH4-M2' and CH4-M2". The mobility of these two co-precipitating proteins is not affected by treatment with 2-mercaptoethanol. It is also noteworthy that the 200 kDa species is present at 0 time. The data indicate that the

TABLE 1

Recognition of IgE classic and IgE (CH4-M2') by anti-constant region and anti-IgE (CH4-M2') antibodies

| | Plates coated with | | Detecting Reagent | | $A_{410\ nm}$ | | |
|---|---|---|---|---|---|---|---|
| | DNS-BSA | CIA-7.12 | CIA-7.12 | α-2331 | IgE Classic | IgE (CH4-M2') | IgG |
| Expt. 1 | + | − | + | − | 2.676 | 0.452 | 0.004 |
| Expt. 2 | − | + | + | − | 2.697 | 0.588 | 0.002 |
| Expt. 3 | − | + | − | + | 0.061 | 1.046 | 0.065 |

IgE classic, IgE (CH4-M2') or IgG were captured on ELISA plates coated with either DNS-BSA or an anti-IgE monoclonal antibody (CIA-7.12) and then detected with either anti-IgE monoclonal antibody (CIA-7.12) or with an anti-serum specific for a sequence unique to IgE (CH4-M2') (α2331). The data shown are the average of duplicate wells. CIA-7.12 is a murine monoclonal antibody recognizing the epsilon heavy chain constant 2/constant 3 domain boundary. α2331 is a rabbit anti-serum generated against a peptide corresponding to the COOH-terminal 10 amino acids of IgE (CH4-M2'). Secondary antibodies were conjugated to alkaline phosphatase. The substrate was p-nitrophenyl phosphate.

IgE Isoform Assembly and Secretion. To dissect the assembly pathways of the various forms of IgE and to determine the efficiency of secretion, pulse-chase experiments were conducted. The classic secreted form of IgE is assembled first to an HL intermediate that is abundant as early as 5 min post-chase. It is later assembled into the $H_2L_2$ form that is detectable 10 min post-chase and abundant within the cells by 20 min post-chase. Very similar kinetics are observed for the assembly of CH4-M2' and CH4-M2". CH4-M2' and CH4-M2" also assemble through an HL intermediate. In addition, for CH4-M2", small quantities of $H_2$ and $H_2L$ are observed intracellularly, and some $H_2$ may be present in the secretion. Those assembly intermediates are minor components of the secreted protein, and are below the level of detection. In all experiments conducted with IgE classic, CH4-M2' and CH4-M2", the intracellular $H_2L_2$ form migrates as a doublet, probably representing IgE at various stages of glycosylation, as the $H_2L_2$ form in the secretions migrates as a single band. Pulse chase experiments conducted with CH4'-CH5 show the only detectable species in the cytoplasm to be light chain and species that migrate as HL half molecules of CH4'-CH5. No free heavy chain is visible, and there is very little assembly to the $H_2L_2$ form.

Fully assembled IgE classic, CH4-M2' and CH4-M2" are detectable in the secretions starting at 60 min post-chase. Quantitative analysis of gels indicates that in the case of IgE classic and CH4-M2', approximately 25% of the total Ig produced during the 5-min pulse is secreted as $H_2L_2$ during the course of the experiment. Following reduction, the secreted proteins migrate as heavy and light chains of approximately 75 and 25 kDa. CH4-M2" is the most efficiently secreted of the isoforms examined, with approximately 40% of the Ig secreted as $H_2L_2$ during the course of the experiment. HL is secreted in varying amounts for each 200 and 50 kDa proteins are not assembly intermediates of IgE but instead represent non-IgE proteins that are co-precipitated. The 200 kDa protein is not secreted, although a band of approximately 50 kDa is seen in the secretions. However, the latter is no longer detectable after treatment with 2-mercaptoethanol, and probably represents light chain dimers. Thus, the co-precipitating 50 kDa protein does not appear to be secreted. FIGS. 3A and 3B show the secretion kinetics.

It has previously been reported that the novel isoforms CH4-M2' and CH4'-CH5 are not secreted by plasma cells. To determine if the cell lines could account for the different results, the expression vector for CH4-M2' described above was transfected into the cell line J558L, the murine myeloma cell line previously used. No positive clones were identified when cell culture supernatants of several hundred selection-resistant transfectomas were screened by ELISA. However, several clones demonstrating high levels of intracellular epsilon chains were identified by ELISA using anti-IgE to capture epsilon chain from cell lysates and alkaline phosphatase conjugated anti-IgE to detect bound epsilon chain. Pulse-chase analysis indicated that large amounts of epsilon chain are produced by this cell line, but are degraded intracellularly. An intracellular HL form was seen by 5 min post-chase, but assembly appeared to stop at this intermediate form, and very little $H_2L_2$ was formed. When these samples were electrophoresed under reducing conditions and analyzed by densitometry, the total intracellular epsilon chain was found to decrease to less than 5% of the original level by 180 min post-chase. The reduced samples also demonstrate the existence of additional, labile species that likely represent degradation products. No $H_2L_2$ is observed in the supernatant of the J558L transfectoma in the same period of time. These results demonstrate that different cell lines may vary in their ability to assemble and secrete the IgE isoforms.

It is evident from the above results, that novel epsilon exon or episilon sequences, transcripts, and translation products have been identified. These products and products derivable therefrom find use in diagnosis, therapy, and drug identification.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A protein composition comprising isolated functional IgE, wherein said isolated functional IgE comprises an epsilon constant region wherein CH4' (SEQ ID NO:2, residues 1–72) is spliced directly to CH5 (SEQ ID NO:3).

2. A polypeptide composition comprising an isolated epsilon constant region wherein CH4' (SEQ ID NO:2, residues 1–72) is spliced directly to CH5 (SEQ ID NO:3).

3. A protein composition comprising isolated functional IgE, wherein said isolated functional IgE comprises an epsilon constant region wherein CH4 (SEQ ID NO:2) is spliced directly to M2" (SEQ ID NO:6).

4. A polypeptide composition comprising an isolated epsilon constant region wherein CH4 (SEQ ID NO:2) is spliced directly to M2" (SEQ ID NO:6).

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 500 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 3..329

(ix) FEATURE:
        (A) NAME/KEY: CDS
        (B) LOCATION: 359..439

(xi) SEQUENCE DESCRIPTION: SEQ ID NO:1:

```
GC CCG CGT GCT GCC CCG GAA GTC TAT GCG TTT GCG ACG CCG GAG TGG        47
   Pro Arg Ala Ala Pro Glu Val Tyr Ala Phe Ala Thr Pro Glu Trp
    1               5                  10                  15

CCG GGG AGC CGG GAC AAG CGC ACC CTC GCC TGC CTG ATC CAG AAC TTC       95
Pro Gly Ser Arg Asp Lys Arg Thr Leu Ala Cys Leu Ile Gln Asn Phe
                20                  25                  30

ATG CCT GAG GAC ATC TCG GTG CAG TGG CTG CAC AAC GAG GTG CAG CTC       143
Met Pro Glu Asp Ile Ser Val Gln Trp Leu His Asn Glu Val Gln Leu
            35                  40                  45

CCG GAC GCC CGG CAC AGC ACG ACG CAG CCC CGC AAG ACC AAG GGC TCC       191
Pro Asp Ala Arg His Ser Thr Thr Gln Pro Arg Lys Thr Lys Gly Ser
        50                  55                  60

GGC TTC TTC GTC TTC AGC CGC CTG GAG GTG ACC AGG GCC GAA TGG GAG       239
Gly Phe Phe Val Phe Ser Arg Leu Glu Val Thr Arg Ala Glu Trp Glu
    65                  70                  75

CAG AAA GAT GAG TTC ATC TGC CGT GCA GTC CAT GAG GCA GCG AGC CCC       287
Gln Lys Asp Glu Phe Ile Cys Arg Ala Val His Glu Ala Ala Ser Pro
80                  85                  90                  95

TCA CAG ACC GTC CAG CGA GCG GTG TCT GTA AAT CCC GGT AAA               329
Ser Gln Thr Val Gln Arg Ala Val Ser Val Asn Pro Gly Lys
                100                 105

TGACGTACTC CTGCCTCCCT CCCTCCCAG GGC TCC ATC CAG CTG TGC AGT GGG       382
                                Gly Ser Ile Gln Leu Cys Ser Gly
                                  1                   5

GAG GAC TGG CCA GAC CTT CTG TCC ACT GTT GCA ATG ACC CCA GGA AGC       430
Glu Asp Trp Pro Asp Leu Leu Ser Thr Val Ala Met Thr Pro Gly Ser
        10                  15                  20

TAC CCC CAA TAAACTGTGC CTGCTCAGAG CCCCAGGTAC ACCCATTCTT                479
Tyr Pro Gln
 25

GGGAGCGGGC AGGGCTGTGG G                                                500
```

(2) INFORMATION FOR SEQ ID NO:2:

(i) SEQUENCE CHARACTERISTICS:
        (A) LENGTH: 109 amino acids
        (B) TYPE: amino acid
        (D) TOPOLOGY: linear     (ii) MOLECULE TYPE: protein         (xi) SEQUENCE DESCRIPTION: SEQ ID NO:2:

```
Pro Arg Ala Ala Pro Glu Val Tyr Ala Phe Ala Thr Pro Glu Trp Pro
 1               5                  10                  15
Gly Ser Arg Asp Lys Arg Thr Leu Ala Cys Leu Ile Gln Asn Phe Met
             20                  25                  30
Pro Glu Asp Ile Ser Val Gln Trp Leu His Asn Glu Val Gln Leu Pro
         35                  40                  45
Asp Ala Arg His Ser Thr Thr Gln Pro Arg Lys Thr Lys Gly Ser Gly
     50                  55                  60
Phe Phe Val Phe Ser Arg Leu Glu Val Thr Arg Ala Glu Trp Glu Gln
 65                  70                  75                  80
Lys Asp Glu Phe Ile Cys Arg Ala Val His Glu Ala Ala Ser Pro Ser
                 85                  90                  95
Gln Thr Val Gln Arg Ala Val Ser Val Asn Pro Gly Lys
                100                 105
```

(2) INFORMATION FOR SEQ ID NO:3:

(i) SEQUENCE CHARACTERISTICS:
        (A) LENGTH: 27 amino acids
        (B) TYPE: amino acid
        (D) TOPOLOGY: linear     (ii) MOLECULE TYPE: protein         (xi) SEQUENCE DESCRIPTION: SEQ ID NO:3:

```
Gly Ser Ile Gln Leu Cys Ser Gly Glu Asp Trp Pro Asp Leu Leu Ser
 1               5                  10                  15
Thr Val Ala Met Thr Pro Gly Ser Tyr Pro Gln
             20                  25
```

(2) INFORMATION FOR SEQ ID NO:4:

(i) SEQUENCE CHARACTERISTICS:
        (A) LENGTH: 700 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 89..172

(ix) FEATURE:
        (A) NAME/KEY: CDS
        (B) LOCATION: 420..446

(xi) SEQUENCE DESCRIPTION: SEQ ID NO:4:

```
CATGGTGGGC ACCCACCTCC AGGGGCCCAG CCAGGGCAGG GGGTTGGGCA GAGCCAGCAG    60

AGCGCCCTGA CCCACGCCCT CCCCTCAG GTG CAG CGG TTC CTC TCA GCC ACG      112
                                Val Gln Arg Phe Leu Ser Ala Thr
                                 1               5
```

```
CGG CAG GGG AGG CCC CAG ACC TCC CTC GAC TAC ACC AAC GTC CTC CAG      160
Arg Gln Gly Arg Pro Gln Thr Ser Leu Asp Tyr Thr Asn Val Leu Gln
    10              15                  20

CCC CAC GCC TAGGCCGCGG GCCACTCACG CTCCACCAGG CCCAGCTTTT              209
Pro His Ala
25

TCTCTGCCAG CGCCTGAGCC TCCCTCGGGC TGCACCCTGC CCTGGGTGGG AAAAGGGAAG    269

CAGACAAGAA AAGGGGGCAC AAGGTCACTA CTGTGGGCTG ATGGCCAGTG AACCTGAGCC    329

CAGAGGGGCC GGCTCAGCCG CAAGGTTACA GGCGCCAGAGA GAACCACCAG TCGCAGGCCC   389

CACCCGAAAA CCGTGTCTGT CCCTTCAACA GAG TCA TCG AGG AGG GGT GGC TGC    443
                                Glu Ser Ser Arg Arg Gly Gly Cys
                                 1               5

TAGCCGTTCT GAGCTCATCC CAGGCCCCTG GGTCTCCGGG TCACTCCCAT TCTGACTGTA    503

CAATCACCAA AAGCCAAGGA GGGCCCGGCA CCCAGCCCAG GGCACAGCTG AGTCTGCGTC    563

CAGCCCAACA CCAGCCCACG GCCTCACTCC CCAGCCTCGG TCTGACCCTT CTAGCCCTGA    623

GATCCAAGTG CCTGGCATCC CCGTCCCCCA AGCCTCACCC AGACCTTCTT TCCCTTCACC    683

CACCCCTCCT GCCACCC                                                   700
```

(2) INFORMATION FOR SEQ ID NO:5:

(i) SEQUENCE CHARACTERISTICS:
        (A) LENGTH: 27 amino acids
        (B) TYPE: amino acid
        (D) TOPOLOGY: linear     (ii) MOLECULE TYPE: protein         (xi) SEQUENCE DESCRIPTION: SEQ ID NO:5:

```
Val Gln Arg Phe Leu Ser Ala Thr Arg Gln Gly Arg Pro Gln Thr Ser
 1               5                  10                  15

Leu Asp Tyr Thr Asn Val Leu Gln Pro His Ala
            20                  25
```

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear     (ii) MOLECULE TYPE: protein         (xi) SEQUENCE DESCRIPTION: SEQ ID NO:6:

```
Glu Ser Ser Arg Arg Gly Gly Cys
 1               5
```

(2) INFORMATION FOR SEQ ID NO:7:

(i) SEQUENCE CHARACTERISTICS:
        (A) LENGTH: 136 amino acids
        (B) TYPE: amino acid
        (D) TOPOLOGY: linear     (ii) MOLECULE TYPE: protein         (xi) SEQUENCE DESCRIPTION: SEQ ID NO:7:

```
Gly Ala Ala Val Pro Leu Ser His Ala Ala Gly Glu Ala Pro Asp Leu
 1               5                  10                  15

Pro Arg Leu His Gln Arg Pro Pro Ala Pro Arg Leu Gly Arg Gly Pro
            20                  25                  30
```

```
Leu Thr Leu His Gln Ala Gln Leu Phe Leu Cys Gln Arg Leu Ser Leu
        35                  40                  45

Pro Arg Ala Ala Pro Cys Pro Gly Trp Glu Lys Gly Ser Arg Gln Glu
        50                  55                  60

Lys Gly Ala Gln Gly His Tyr Cys Gly Leu Met Ala Ser Glu Pro Glu
65                  70                  75                  80

Pro Arg Gly Ala Gly Ser Ala Ala Arg Leu Gln Ala Pro Arg Glu Pro
                85                  90                  95

Pro Val Ala Gly Pro Thr Arg Lys Pro Cys Leu Ser Leu Gln Gln Ser
            100                 105                 110

His Arg Gly Gly Val Ala Ala Ser Arg Ser Glu Leu Ile Pro Gly Pro
        115                 120                 125

Trp Val Ser Gly Ser Leu Pro Phe
        130                 135

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

TCATGCGGTC CACGACCAAG A                                          21
```